US005731055A

United States Patent [19]

Bernardo

[11] Patent Number: 5,731,055

[45] Date of Patent: Mar. 24, 1998

[54] 100% POLYESTER MATERIAL FOR THE MANUFACTURE OF A PEST CONTROL APPLICATOR

[75] Inventor: Marie Cristina Spada Bernardo, Sao Paulo, Brazil

[73] Assignee: Casa Bernardo LTDA, Sao Paulo, Brazil

[21] Appl. No.: 393,137

[22] Filed: Feb. 21, 1995

Related U.S. Application Data

[63] Continuation-in-part of Ser. No. 995,628, Dec. 21, 1992, abandoned.

[51] Int. Cl.[6] .................... B32B 1/04; B32B 3/02; A01M 13/00; A01M 1/20

[52] U.S. Cl. .................... 428/76; 428/70; 428/74; 428/96; 428/480; 43/125; 43/131; 43/132.1

[58] Field of Search .................... 428/74, 76, 70, 428/96, 480; 43/125, 131, 132.1

[56] References Cited

U.S. PATENT DOCUMENTS 4,205,028 5/1980 Brueggemann et al. .................... 428/70

4,597,218 7/1986 Friemel et al. .................... 428/76

4,932,155 6/1990 Friemel et al. .................... 428/76

*Primary Examiner*—Patrick Ryan

*Assistant Examiner*—Cathy F. Lam

*Attorney, Agent, or Firm*—Armstrong, Westerman, Hattori, McLeland & Naughton

[57] ABSTRACT

Gas-permeable 100% reinforced thermosetting polyester film material for the manufacture of pest control applicators, comprising a grid including a base of polyester yarn overlain with top and bottom layers of polyester fibers, and an aqueous-based paste of the same polyester filling the spaces between the grid yarn and fibers and having a melting point lower than the grid yarn and fibers polyester. A pest control applicator is formed of such film material, filled with pest control agent reactive with water to release a fumigating gas, and after reaction of the pest control agent with air humidity, the applicator is immersed in water to deactivate residial pest control agent.

9 Claims, 2 Drawing Sheets

4

100% POLYESTER MATERIAL FOR THE MANUFACTURE OF A PEST CONTROL APPLICATOR

BACKGROUND OF THE INVENTION

This application is a continuation-in-part of application Ser. No. 07/995,628, filed Dec. 21, 1992, now abandoned, in the name of the same inventor, for 100% Polyester Reinforced Material for the Manufacture of Pest Control Applicator.

1. Field of the Invention

This invention relates to a 100% polyester reinforced material in the form of a laminated film to hold a pest control agent, and process for the manufacture of a laminated film. The application also relates to an applicator formed from such reinforced, laminated film and containing a fumigating agent for the control of pests which may be found in grain, processed food, animal fodder, non-edible manufactured goods such as wood and others stored in warehouses, silos, holds of vessels, boats, wagons, etc. An outstanding feature of the invention is that it ensures the release of phosphine gas through reaction with air humidity of the fumigation agent, preferably a solid or powdered metallic phosphide, contained in the applicator. Due to the innovative features of the laminated film intrinsic to the final applicator, a highly improved fumigation efficiency rate and subsequent removal of toxic residue is achieved in comparison with similar films and applicators to which the field often resorts.

2. Description of Related Art

It is well known that grain storage, whether simple storing in warehouses, silos and such, or through carriage in vessels and such craft, must necessarily rely on an efficient means of disinfecting of any pests found therein, which is generally done by using a fumigating product, in particular a metallic phosphide, preferably aluminum phosphide, hydrolyzable through the action of air humidity, which reaction triggers the release of the toxic gas phosphine which is lethal to pests until substantially the entire phosphide content is released. To this end, the premises must be kept tightly closed and only be opened after the gas activity period has elapsed. In such ideal application conditions, the pesticide agent is packed, as various measured doses, inside a gas and humidity-permeable wrapping.

In view of the toxic nature of the metallic phosphide, it is required that no direct contact between the latter and the grain occurs, and to this end, one of the methods of distribution in the bulk of the grain is the parcelling out of small envelopes or bags, known in the market as "sachets", each containing a predetermined quantity of metallic phosphide, preferably aluminum phosphide, as required for the efficient disinfestation of the premises.

The aforementioned sachets must necessarily possess certain characteristics to achieve the desired effect. Thus they are made, according to the present state of the art, from material such as paper, non-woven from a cellulose base, or certain synthetic polymers of multiple types. Among the most common examples of such elements, there can be mentioned polyamide, polyesters, and polyacrylic compounds, particularly polyacrylamide, as well as glass fibers, or other sealing materials with a lower melting or softening point.

Characteristics pertaining to the material used are vitally important in the case of an applicator as described, not only with regard to the closing, but also with regard to essential factors such as humidity and gas permeability, porosity, mechanical resistance, among others, which keep present manufacturers and researchers in the search for constant improvement.

Thus, recently the state of the art learned of a sachet made from TYVEK, a synthetic polymer manufactured by DU PONT, composed of 100% high density polyethylene fibers and a second sealing component. An example of this development is Brazilian patent application 8802477.

Insofar as a general study of the state of the art is concerned, it can be said that the envelope, or paper sachet, one of the first to be developed, is sewn next to the borders with a view to providing a fully sealable and air permeable packaging, in order to allow for the occurrence of the aluminum phosphide reaction, so as to release phosphine gas.

However, use of a product such as paper results in some drawbacks in the finished packaging, namely in the applicator, such as smaller physical resistance and durability, particularly if one considers that such envelopes generally remain under tons of grain, therefore subject to heavy compressive and tensile stress, and tearing. Another negative point is that the packaging sewn or glued next to the border, may allow for leaking of aluminum phosphide, especially through the seams, placing the product in direct contact with the grain, which is undesirable.

With regard to sachets made from a non-woven material with a cellulose base and/or from multiple component synthetic polymers, comprising at least one film-forming material to form fibers with a melting or softening point above 165 degrees Centigrade and a second material with thermoplastic properties and a melting or softening point below 145 degrees Centigrade, or within the ranges 180 to 235 degrees Centigrade and 80 to 120 degrees Centigrade, respectively, these have limited physical characteristics and during use, may tear or break open, releasing highly toxic aluminum phosphide which will come into direct contact with the grain undergoing fumigation.

On the other hand, proofers used on synthetic fabrics do not form an even layer during the application procedure, resulting in a disproportionate release of phosphine which hinders fumigation and delays water penetration thus requiring that the fumigant package be placed in a container with water to accelerate residual phosphide reaction.

With regard to 100% high or low density polyethylene synthetic fabrics, coated on one side with thermoplastic adhesive, they show, like the previous ones, the drawback of other non-woven materials, especially with regard to disproportionate release of phosphine, rendering the phosphine gas concentrations very low, particularly close to the sachet surface. Besides, because of the characteristic of impermeability of this material, it is rendered less efficient when, upon completion of fumigation, it is necessary to neutralize the residual aluminum phosphide by immersion in water.

SUMMARY OF THE INVENTION

In view of these and other drawbacks, the inventor envisaged the present material, obtained through its own particular process, resulting in a laminated sheet with improved properties for usage as an applicator for hydrolyzable phosphides utilized in fumigating different enclosures; this laminated material differing from prior materials used for such purposes in that it is basically made up from a polymerized reinforced non-woven 100% polyester, with its own self-thermosealing characteristics and therefore not requiring the use of glues, pasting, agglutinant or other adhesive substances.

The laminated material in question, aside from preserving the physical properties necessary to an efficient performance in the use of metallic phosphide, for example aluminum phosphide, in the disinfecting of grain and others, such as permeability to air humidity and phosphine gas release, retention of aluminum phosphide powder and aluminum hydroxide residue powder, after phosphine is released in full, possesses physical characteristics superior to those of sachets made from paper, compound cellulose with synthetic fibers, and the 100% high density polyethylene sachet, such as TYVEK. The 100% polyester synthetic polymer is more tear-resistant, both crosswise and lengthwise, which is also the case under tensile stress and friction.

Besides all these aspects, an essential characteristic of the laminated material of the invention and which makes it stand out from the others is the water permeability rendering possible the deactivating of the aluminum phosphide final residue, as well as the fact that it is self-thermosealable with conventional equipment. This water permeability is an advancement vis-a-vis previous inventions, due to the need for deactivating the residue prior to disposal of material after its application to control insects found in stored grain, foodstuffs, etc.

The above characteristic is due to the fact that in every fumigation procedure, upon completion of application, a solid residual ingredient (nearly imperceptible) remains intact inside the sachet after exposure. Basically, there are two methods of disposing of this residue, viz:

through airing of bags or sachets in the open air until the entire reaction is completed;

through water deactivating.

Thus, in the particular case of a conventional two-component sachet, the main one being non-woven 100% high density polyethylene (TYVEK) with sealant, the same is water resistant and, in order to accomplish water deactivating, it becomes necessary to open the sealed parts and literally discharge the residual powder in the water. Besides increasing contact of persons in charge of application with the toxic powder, this renders the procedure extremely slow if water deactivating is to be contemplated.

It is worthwhile mentioning in this regard, that according to conventional disposal techniques, when gas is released in the atmosphere, it pollutes the environment and water deactivating was conceived to try and eliminate the problem. However, difficulties encountered in such deactivating with applicators made of certain materials did not achieve a final solution.

Another important feature is that the material in question possesses fibers rendering it recyclable.

This invention therefore aims at a material especially conceived to accomplish with maximum efficiency all the functions pertaining to the various fumigation stages in different enclosures, eliminating problems, step by step. To that end, a process was created to achieve a laminated single-component material, self-thermosealable and which can be used as an applicator for the fumigation of pests with high efficiency, safety and disposal of residues.

The material developed is basically 100% polyester obtained by a process requiring the use of a grid of reinforcement fibers and paste with the same original chemical base, namely polyester, processed in accordance with specific steps, so as to achieve a laminated material having the particular characteristic described and which, from a technical point of view, is ideally suited for use as a fumigating applicator.

Thus, another purpose of the invention is to provide a reinforced 100% polyester, self-thermosealable laminated material.

A third purpose is to form an applicator as a bag or sachet, which can, after application, be placed in a container with water without requiring opening for deactivating, thus allowing water to come into contact with residual powder for a complete and safe deactivation.

Therefore this invention contemplates, among others, increased safety of persons in charge of applying powder pesticides and during deactivating of the same. In addition to that, it is rendered less harmful to the environment, since it opens up the possibility of entirely safe water deactivating, replacing the aeration of toxic gases into the atmosphere or physical contact with residual powder. Further upon incineration, the material contemplated in this invention basically generates carbon dioxide and water.

Another positive feature of this invention is that it includes a fiber and paste adaptation which renders the resulting material biodegradable, accomplishing the task of providing safety not only to the person involved in the application, but also to the environment.

Insofar as application is concerned, the material herein claimed can also be employed in the manufacture of gas-absorbing "pads", in this case of phosphine gas, for use in tightly sealed flasks or tins, meant for absorption of any gas eventually produced inside the packaging. Such "absorbent pads" are made of the same material as the applicator and should contain a mixture of nontoxic chemical powder, with the property of absorbing any gases eventually found in the flasks or containers. This characteristic also provides safety to the product user, insofar as carriage and warehousing is concerned.

BRIEF DESCRIPTION OF THE DRAWINGS

Below, the invention is explained in greater detail and for better understanding, the attached drawings should be referred to as follows.

DESCRIPTION OF PREFERRED EMBODIMENTS

Figure 1:
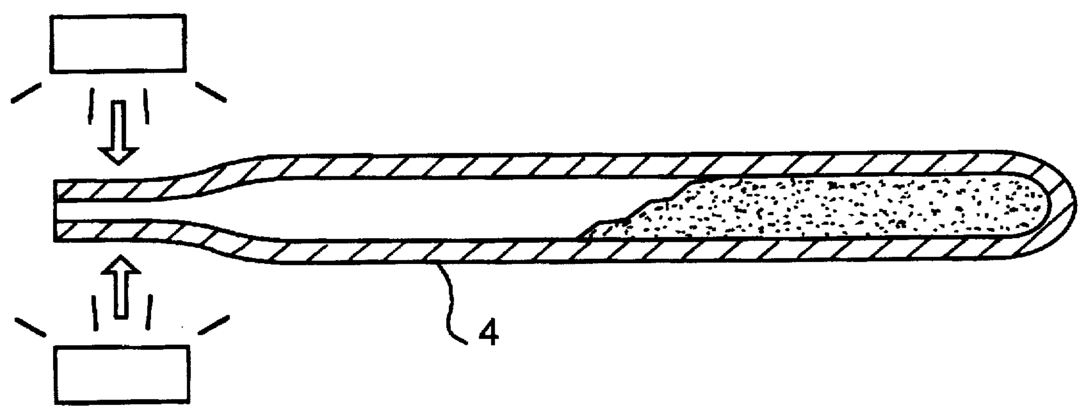
FIG. 1 is a section side view of an applicator sachet, during preparation, showing the self-thermosealing stage.
Figure 2:
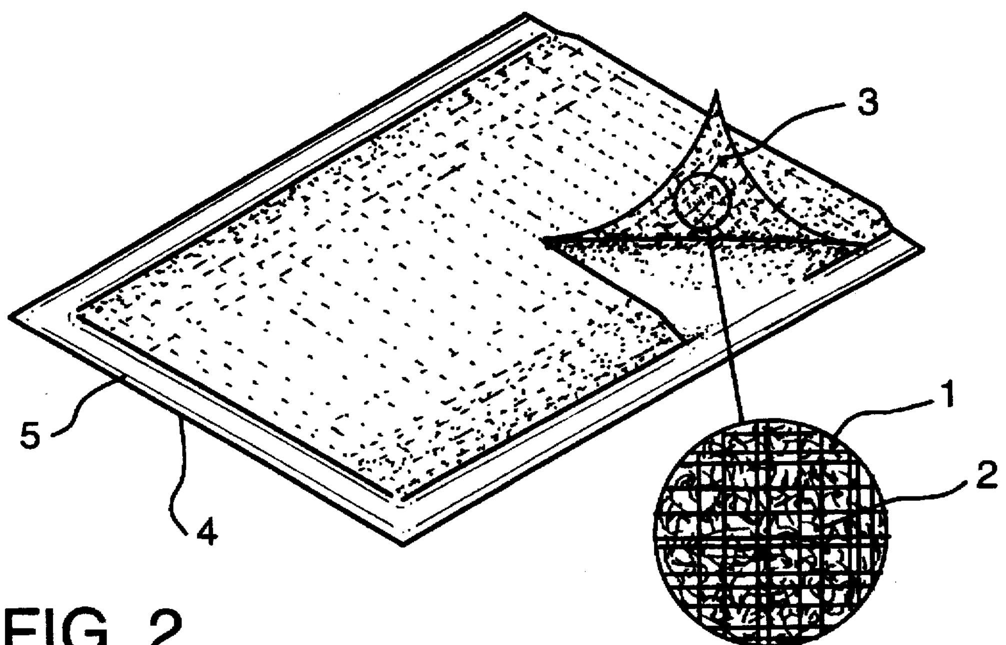
FIG. 2 is a perspective view of an applicator sachet, with enlarged details of material.

The reinforced 100% polyester material for the manufacture of laminated film to form an applicator for holding a pest control agent basically consists of a material noteworthy for having a single component base, that is, 100% thermosetting polyester, with reinforcing grid fibers having a melting or softening point of 200 to 280 degrees Centigrade, more particularly between 220 and 270 degrees Centigrade, and a paste with thermosetting properties of the same polyester component but having a different molecular arrangement and with a melting or softening point of 80 to 160 degrees Centigrade, more particularly between 120 and 135 degrees Centigrade.

The reinforced material of the invention comprises a reinforcing grid composed of fully polymerized polyester yarn (1) with a diameter of 0.5–10 microns and present in a weight per unit area of 8 to 40 g/m$^2$, preferably 15 to 25 g/m$^2$; and smaller, fully polymerized polyester fibers (2) with a diameter of 1 to 6 dTex, preferably 1.3 to 3.3 dTex, present in a concentration of 30 to 70 g/m$^2$, preferably 50 to 55 g/m$^2$.

The self-sealing characteristic of the material is ensured by the use of a thermosetting paste (3) composed of the same original chemical base as the grid fibers, that is, polyester copolymer, the paste being formed by an aqueous dispersion of the polyester copolymer, with a melting or softening point of 80 to 160 degrees Centigrade, and present in a concentration of 5 to 50 g/m$^2$, preferably 15 to 20 g/m$^2$.

The material as described is obtained through polymeric synthesis of terephthalic acid monomers with ethylene glycol. By varying the synthesis conditions, copolymers having different molecular arrangements and, consequently, different softening or melting points, can be obtained.

The use of larger yarn strands (1) and smaller fibers (2) overlying the yarn strands on the top and bottom thereof provides better straightening and hence better bonding between the grid fibers and the paste (3).

For the making of the laminated film, achieved through a continuous process of physical linking, the grid has its yarn fibers (1), 0.5 to 10 microns in diameter, covered by upper and lower coatings of a mixture of smaller fibers (2), of 1–6 dTex, prefereably 1–3 dTex diameter, with spaces between the reinforcing fibers being filled with paste (3). Bonding of the paste (3) to grid fibers (1) and (2) occurs by means of pressure and heat (thermobonding), at 80 to 160 degrees Centigrade, more especially, between 120 and 135 degrees Centigrade.

Laminated film (4) thus obtained shows, as a fundamental characteristic, the use of a single component basic product, i.e., polyester, reinforced and porous, besides showing high mechanical resistance, being heat and pressure self-thermosealable within the range of 80 to 160 degrees Centigrade, and enjoying the special feature of not losing its physical characteristics either in the area of the softening point or when wet, while its air permeability is 5 to 25 m$^3$/m$^2$-minutes, preferably 12 to 15 m$^3$/m$^2$-minutes, containing no thermosealable adhesive.

An applicator obtained from this laminated material may be used in the manufacture of envelopes, bags, sachets, interlinked or otherwise, in any geometrical shape, to hold hydrolyzable metal phosphide, for example aluminum phosphide, and with flexible connections. In addition, other chemical or pharmaceutical products with the desirable gas and humidity permeable properties and high mechanical resistance can benefit from its use.

Thus the applicator is novel in that it is a sachet for a pesticide compound, made of a gas and water vapor permeable non-woven, water-free material which differs in that it has one single component, 100% polyester, with reinforcing grid fibers having a softening or melting point between 200 and 280 degrees Centigrade, more particularly between 220 and 270 degrees Centigrade, and a copolymer paste with the thermosetting properties of the same component, polyester, but with a melting or softening point of 80 to 160 degrees Centigrade, more particularly of 120 to 135 degrees Centigrade.

As a final product, the applicator has air permeability of 5 to 25 m$^3$/m$^2$-minutes, more precisely 10 to 18, and best 12 to 15 m$^3$/m$^2$-minutes.

The applicator stands out for use with a pest control agent in solid, granulated or powder form, and is obtained by thermobonding, through pressure, of two layers of laminated film (4), particularly by border sealing (5) in an area of at least 1 cm. In other words, the same thermosetting material in the form of paste (3) works to render possible the formation of bonding seams over the entire surface of the product, as desired, in order to ensure permeability to phosphine gas and to air humidity, and to maintain the capacity of retention of aluminum phosphide, as well as of fine powdered aluminum hydroxide resulting from phosphide reacting with humidity.

The desired sealing and powder retention of sachets obtained according to this invention is due to the fact that the intermediate gaps between the fibers of the higher melting point component, are filled by the same but lower melting point paste (3) component.

As stated before, an applicator obtained in accordance with the laminated material of this invention facilitates water penetration at the time of disposal of residual aluminum phosphide, resulting in safety and efficiency in this operation, that is, providing the means for water deactivating to become fully feasible.

For a better understanding of the contribution of this invention to the state oft he art, it can be said that porosity of the polyester non-woven material is such that gases can pass through without difficulty, although powder, as is the case upon hydrolysis of pesticide compounds, has its passage blocked. Speaking in figures, it can be said that the non-woven pore sizes are quite suitable, that is, more than 0.25 mm, particularly 0.20 to 0.40 mm and preferably between 0.25 and 6.38 mm, which figures in practice prevent pesticide compounds residue from escaping.

A dye may also be introduced in the fiber-forming material; preferably sachets may be dyed in such a way as to receive on being used a clear reference to place of manufacture and, based on previous market experience, a reference to contents.

Naturally, it also works to advantage to have the name of the pesticide, directions for use and warnings about the pesticides or other products printed on the sachet. Printing is a toxic since it is water soluble and dries instantly.

Weight per square meter of material is preferably between 40 and 100 g/m$^2$, the higher limit being determined before the material loses its required flexibility. According to a special invention procedure, specific weight, or weight per square meter, is preferably 80 to 100 g/m$^2$ and more particularly, 70 to 95 g/m$^2$.

For the manufacture of the sachet or applicator, according to the invention, a piece of the laminated material (4) may be folded and sealed along the sides. Through the remaining opening, the solid, granulated or powdered pesticide may then be poured in. Thereafter, the remaining opening is also closed with special equipment.

Figure 3:
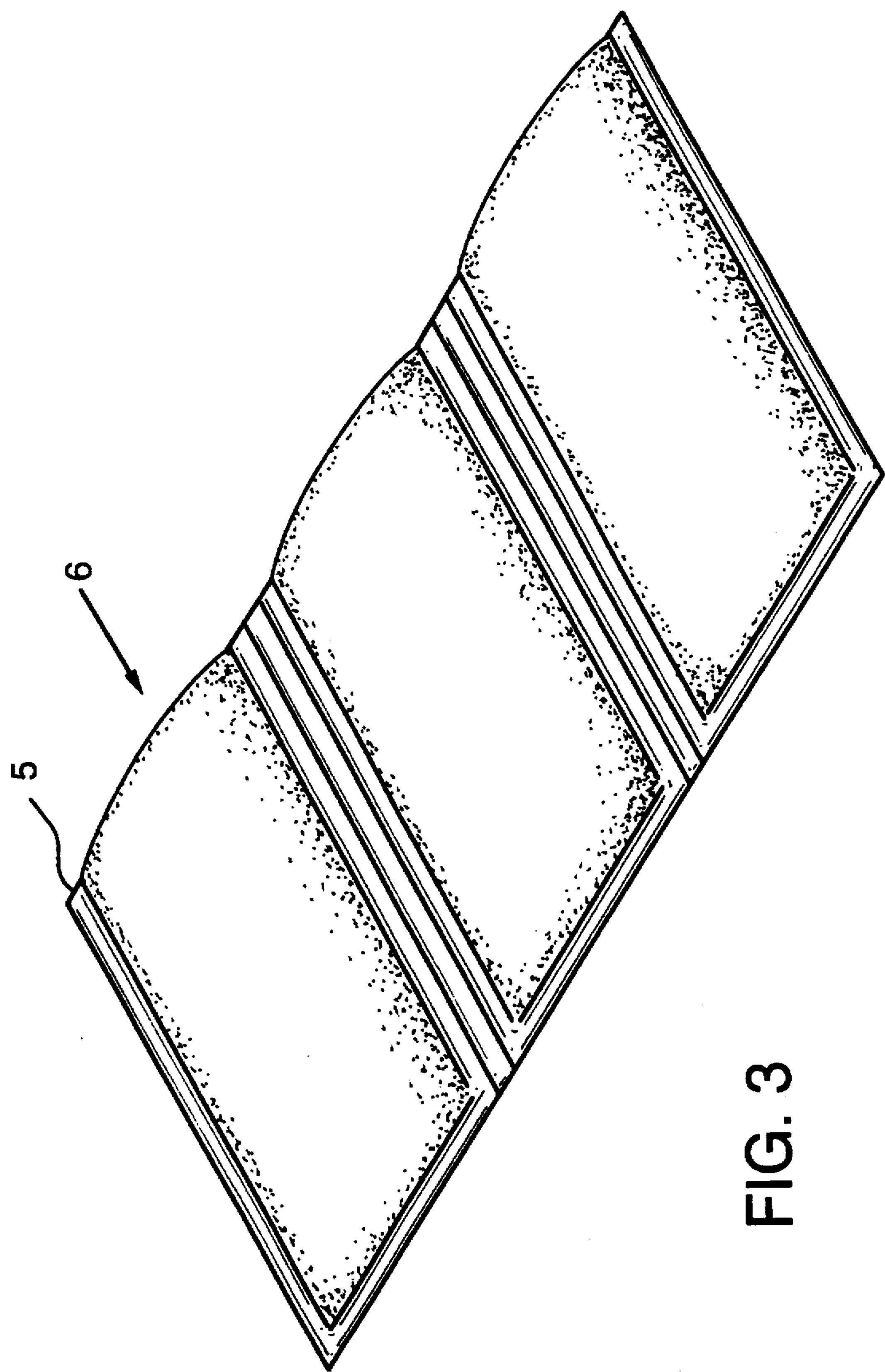
FIG. 3 is a perspective view of applicator sachets showing an example of serial placement or strips.

Another possibility, as shown in FIG. 3, is the manufacture of the applicator sachet (6) in an automatic bagging machine for serial tube bags, already available in the state of the art. Naturally, in general, it is especially convenient for the manufacture and/or filling of bags, according to the invention, to use devices which are found in the market in various forms. Thus, for example, suitable automatic devices may be found, based on heat and pressure sealing or ultrasound sealing.

Laminated material claimed may be used for the manufacture of square, rectangular or tubular sachets or of any other geometrical form, interlinked or otherwise, with no limitation on dimensions, such as length, width, quantity of interlinked bags which may vary according to the application and application characteristics.

After closing the bag, in accordance with the invention, the pesticide compound is completely closed in, while the powder resulting from its decomposition, can no longer escape from the mentioned bag which, holding the pesticide, may be placed right into the foodstuffs about to be fumigated.

Special packaging is used for storage and transportation of sachets in a safe and practical way, avoiding contact with air humidity, prior to their application as pest control applicators.

In addition, the material may be used as a gas absorber, such as phosphine, making up "pads" for use in hermetically sealed flasks, such pads being made of the same material as the bags, with a mixture of chemical non-toxic powder for the absorption of gases found in flasks, containers or other kinds of packing.

PRACTICAL TESTS

The applicator bag containing the pesticide manufactured with the 100% polyester non-woven polymer was submitted to some practical tests so as to verify its behavior under possible misuse.

The bags, according to the invention, were filled with 34 g of aluminum phosphide. Results were as follows:

DRIP TEST

A bag was placed in a glass vat of 2-liter capacity. Through a drip funnel, water at 70 degrees Centigrade was dripped onto the bag during one hour, at the rate of one drop per second. Test was performed at room temperature; no ignition occurred in the bag.

SPRINKLE TEST

A bag was placed in a glass vat of 2-liter capacity; 10 ml of water, at room temperature, were sprayed on same by means of a sprinkler. For the full extent of one hour, the bag was sprayed every fifteen minutes with 10 ml of water. Test was performed at room temperature; no ignition occurred in the bag.

BATH TEST

A bag was placed in a metallic container and water at room temperature added until the bag was covered. Test was performed at room temperature and it was found that, after four hours, no ignition occurred in the bag.

POWDER TEST 15 grams of aluminum phosphide in powder form were weighed and placed in 1 150 ml narrow-shaped beaker. The whole was then heated up to 50 degrees Centigrade, by means of an electric heater. Upon reaching a temperature of 35 degrees Centigrade, 5 ml of water at room temperature were added with a pipette. The beaker was left to rest for an hour at room temperature and no ignition of the bag occurred.

Proof of the better physical quality of the bag material, contemplated under this invention, as compared with other existing materials, can be ascertained from the results of tests performed, in accordance with the following table:

| | Non-woven 100% Polyester | Non-woven 100% polyethylene | Non-woven Cellulose/ Fiber |
|---|---|---|---|
| Weight/area ($g/m^2$) | 95 | 75 | 87 |
| Thickness (mm) | 0.170 | 0.210 | 0.300 |
| Resistance (kgf/5cm) Stretching (%) Breaking point Lengthwise | 36/30 | 38/60 | 19/24 |
| Resistance (kgf/5cm) Stretching (%) Breaking point Crosswise | 26.5/33 | 45/70 | 3.8/35 |
| Tear resistance (kgf) Lengthwise | 8.4 | 1.60 | 0.25 |
| Tear resistance (kgf) Crosswise | 7.7 | 2.00 | 0.45 |
| Abrasion 1,000 cycles; strain 1 $kgf/cm^2$ lengthwise | | | |

None of the materials showed wear.

What is claimed is:

1. A pest control applicator formed of a gas-permeable reinforced non-woven 100% polyester self-sealing film material comprising a grid consisting of fibers of a thermosetting polyester, and an aqueous-based paste with thermosetting properties of the same original chemical base as the grid fibers but having a different molecular arrangement, and having a melting or softening point lower than the thermosetting polyester of the grid fibers, said paste filling the spaces between the grid fibers and heat and pressure bonded to the grid fibers.

2. A pest control applicator formed of a gas-permeable reinforced non-woven, 100% polyester self-sealing film material comprising a grid including a base of thermosetting polyester yarn and top and bottom layers of fibers of the same thermosetting polyester overlying the base yarn, and an aqueous-based paste filling spaces between the grid yarn and fibers and with thermosetting properties of the same original chemical base as that forming the yarn and fibers but having a different molecular arrangement and a melting or softening point lower than the yarn and fiber polyester and heat and pressure bonded to the grid yarn and fibers.

3. An applicator according to claim 2, wherein the yarn has a diameter of about 0.5 to 10 microns and the overlying fibers have a diameter of about 1–6 dTex.

4. An applicator according to claim 2, wherein the polyester is a copolmer of terephthalic acid monomers and ethylene glycol.

5. An applicator according to claim 4, wherein the grid yarn and fiber polyester has a melting point of about 200 to 280 degrees Centigrade and the paste polyester has a melting point of about 80 to 160 degrees Centigrade.

6. An applicator according to claim 3, wherein the polyester is a copolymer of terephthalic acid monomers and ethylene glycol.

7. An applicator according to claim 6, wherein the grid yarn and fiber polyester has a melting point of about 200 to 280 degrees Centigrade and the paste polyester has a melting point of about 80 to 160 degrees Centigrade.

8. An applicator according to claim 7, wherein the base yarn is present in a weight per unit area of film material of about 8 to 40 $g/m^2$, the overlying polyester fibers are present in a weight per unit area of film material of about 30 to 70 $g/m^2$, and the polyester paste is present in a weight per unit area of film material of about 5 to 50 $g/m^2$.

9. A pest control applicator according to one of claims 1–8, wherein the film material has an air permeability of about 5 to 25 $m^3/m^2$-minutes.

* * * * *